(12) United States Patent
Ensign

(10) Patent No.: US 7,727,281 B2
(45) Date of Patent: Jun. 1, 2010

(54) MODULAR FEMORAL KNEE STEM EXTENDER

(75) Inventor: Michael D. Ensign, Salt Lake City, UT (US)

(73) Assignee: Ortho Development Corporation, Draper, UT (US)

(*) Notice: Subject to any disclaimer, the term of this patent is extended or adjusted under 35 U.S.C. 154(b) by 1227 days.

(21) Appl. No.: 11/284,787

(22) Filed: Nov. 21, 2005

(65) Prior Publication Data
US 2006/0173547 A1 Aug. 3, 2006

Related U.S. Application Data

(63) Continuation-in-part of application No. 11/136,089, filed on May 23, 2005, now abandoned, which is a continuation of application No. 11/008,783, filed on Dec. 8, 2004, now abandoned.

(60) Provisional application No. 60/527,970, filed on Dec. 8, 2003.

(51) Int. Cl.
A61F 2/38 (2006.01)

(52) U.S. Cl. .............. 623/20.15; 623/20.14; 623/20.35; 623/20.36

(58) Field of Classification Search .............. 623/16.11, 623/17.17–23.63; A61F 2/38
See application file for complete search history.

(56) References Cited

U.S. PATENT DOCUMENTS

| | | | |
|---|---|---|---|
| 4,224,697 A | 9/1980 | Murray et al. |
| 4,714,471 A | 12/1987 | Grundei |
| 4,822,366 A | 4/1989 | Bolesky |
| 4,936,847 A | 6/1990 | Manginelli |
| 4,985,037 A | 1/1991 | Petersen |
| 5,133,760 A | 7/1992 | Petersen et al. |
| 5,147,406 A | 9/1992 | Houston et al. |
| 5,152,796 A | 10/1992 | Slamin |
| 5,258,032 A | 11/1993 | Bertin |
| 5,326,359 A | 7/1994 | Oudard |
| 5,330,534 A | 7/1994 | Herrington et al. |
| 5,556,433 A | 9/1996 | Gabriel et al. |
| 5,683,472 A | 11/1997 | O'Neil et al. |
| 5,702,460 A | 12/1997 | Carls et al. |
| 5,766,255 A | 6/1998 | Slamin et al. |
| 5,824,097 A | 10/1998 | Gabriel et al. |
| 5,879,391 A | 3/1999 | Slamin |
| 5,944,756 A | 8/1999 | Fischetti et al. |
| 6,071,311 A | 6/2000 | O'Neil et al. |
| 6,090,146 A | 7/2000 | Rozow, III et al. |
| 6,126,693 A | 10/2000 | O'Neil et al. |

(Continued)

Primary Examiner—David Isabella
Assistant Examiner—Yashita Sharma
(74) Attorney, Agent, or Firm—Matthew D. Thayne; Stoel Rives LLP (57) ABSTRACT

A knee prosthesis includes a femoral component and a stem for implanting in a femur. A modular junction is provided for attaching the stem to the femoral component. The femoral component may include a boss having a slot for receiving the components of the modular junction. A portion of the modular junction may be placed within the slot and the modular junction may be tightened in place on the boss by threading the stem into engagement with a portion of the modular junction. Accordingly, the stem may be connected to the femoral component by a single threaded engagement and the position of the stem may be adjusted to any desired location along the anterior-posterior direction on the femoral component.

21 Claims, 6 Drawing Sheets

U.S. PATENT DOCUMENTS

| | | |
|---|---|---|
| 6,171,342 B1 | 1/2001 | O'Neil et al. |
| 6,214,052 B1 | 4/2001 | Burkinshaw |
| 6,413,279 B1 | 7/2002 | Metzger et al. |
| 6,503,254 B2 | 1/2003 | Masini |
| 6,527,807 B1 | 3/2003 | O'Neil et al. |
| 6,589,283 B1 | 7/2003 | Metzger et al. |
| 6,613,092 B1 | 9/2003 | Kana et al. |
| 6,629,999 B1 | 10/2003 | Serafin, Jr. |
| 2002/0040244 A1 | 4/2002 | Despres, III et al. |
| 2002/0120340 A1 | 8/2002 | Metzger et al. |
| 2003/0009232 A1 | 1/2003 | Metzger et al. |
| 2003/0204263 A1 | 10/2003 | Justin et al. |
| 2003/0204264 A1* | 10/2003 | Stumpo et al. ............ 623/20.36 |

* cited by examiner

MODULAR FEMORAL KNEE STEM EXTENDER

CROSS-REFERENCE TO RELATED APPLICATIONS

This application is a continuation-in-part of U.S. patent application Ser. No. 11/136,089, filed May 23, 2005 now abandoned, entitled "MODULAR FEMORAL KNEE STEM EXTENDER," which is a continuation of U.S. patent application Ser. No. 11/008,783, filed Dec. 8, 2004 now abandoned, entitled "MODULAR FEMORAL KNEE STEM EXTENDER," which claims the benefit of U.S. Provisional Application No. 60/527,970, filed Dec. 8, 2003, all of which are hereby incorporated by this reference herein in their entireties, including but not limited to those portions that specifically appear hereinafter, the incorporation by reference being made with the following exception: In the event that any portion of the above-referenced applications is inconsistent with this application, this application supercedes said above-referenced applications.

STATEMENT REGARDING FEDERALLY SPONSORED RESEARCH OR DEVELOPMENT

Not Applicable.

BACKGROUND

1. The Field of the Invention

The present disclosure relates generally to prostheses, and more particularly, but not necessarily entirely, to knee prostheses having adjustable modular components.

2. Description of Related Art

Joint prostheses having modular components are known for use in repairing damaged or diseased knee joints. A knee joint is primarily formed by two bones, namely an upper bone or femur and a lower bone or tibia. Knee joint prostheses typically include a femoral component configured and arranged for insertion into a canal of the femur and a tibial component configured and arranged for insertion into a canal of the tibia. The femoral component may be attached to a stem that may be received into the femur of a patient to improve the stability of the prosthesis. The modular features of the prosthesis allow different sized or configured portions of the prosthesis to be used so that the prosthesis can be properly placed in patients having bones of different sizes and anatomical variations. For example, an anatomic axis may be defined by the axis of the femur, and a mechanical axis may extend from the center of the condyles in the femoral component up through the hip. A valgus angle may be formed between the anatomic axis and the mechanical axis. The valgus angle may be different for different people, for example, ranging between about 5 degrees and about 10 degrees. By providing a modular prosthesis, different stems may be attached to the femoral component at different locations to accommodate different valgus angles.

Moreover, the modularity of the prostheses may allow a reduction of prostheses inventory in that certain components of the prostheses may be used for numerous patients of various sizes and anatomical variations, and only particular portions of the prostheses may need to be selected to properly fit an individual patient.

A drawback of the known modular prostheses is that the adjustment capabilities of the modular components may be limited. The modular components may be fixed to the prostheses in a finite number of locations or orientations. Thus, if a particular anatomical structure does not conform to the possible configurations of the particular prosthesis, a precise fit of the prosthesis cannot be achieved. Moreover, modular prostheses often have complex attaching mechanisms that make assembling the prostheses difficult and time consuming.

The prior art is thus characterized by several disadvantages that are addressed by the present disclosure. The present disclosure minimizes, and in some aspects eliminates, the above-mentioned failures, and other problems, by utilizing the methods and structural features described herein.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 6b is a side view of a modular junction extending in a second direction at an angle with respect to the modular junction of FIG. 6a;

DETAILED DESCRIPTION

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise. Also, as used herein, the terms "comprising," "including," "containing," "characterized by," and grammatical equivalents thereof are inclusive or open-ended terms that do not exclude additional, unrecited elements or method steps.

As used herein, the term "proximal" shall refer broadly to the concept of a nearest portion. Similarly, as used herein, the term "distal" shall generally refer to the opposite of proximal, and thus to the concept of a further portion, or a furthest portion, depending upon the context.

Figure 1:
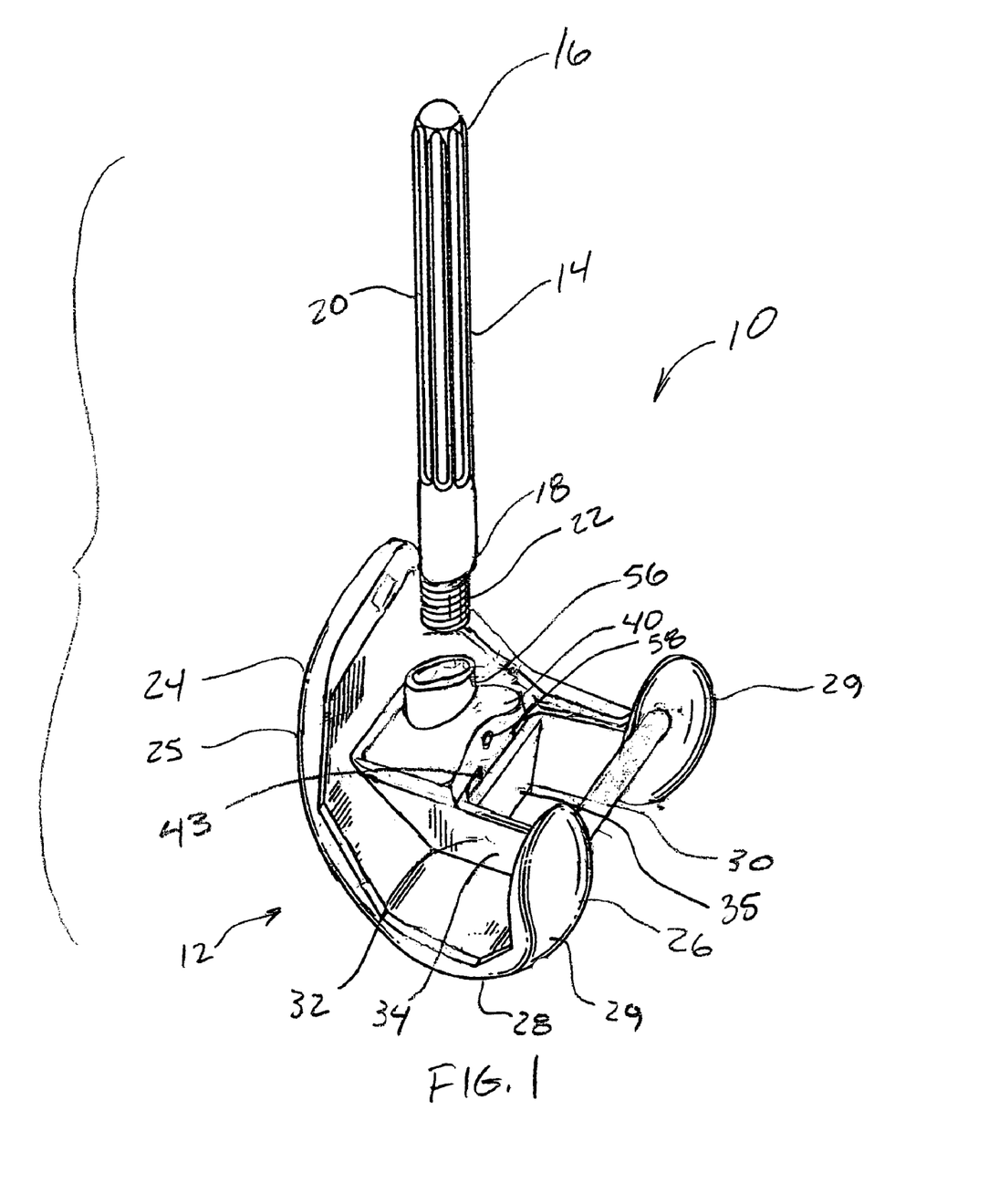
FIG. 1 is an exploded perspective view of a prosthetic device made in accordance with the principles of the present disclosure.

Referring now to FIG. 1, an exploded perspective view is shown of a prosthetic device, indicated generally at 10. The prosthetic device 10 may be used in conjunction with a tibial component (not shown), for use in repairing a diseased or damaged knee joint. It will be appreciated that a knee joint is primarily formed between an upper leg bone or femur and a lower leg bone or tibia. The tibial component may be positioned on a proximal end of the tibia, whereas the prosthetic device 10 of the present disclosure may be positioned on a distal end of the femur.

The prosthetic device 10 may include a femoral component, indicated generally at 12, and a stem 14. The stem 14 may include a proximal portion 16 and a distal portion 18. The proximal portion 16 of the stem 14 may be configured to be received in a cavity formed in the intramedullary canal of the distal end of the femur to provide stability to the prosthetic device 10. The stem 14 may be configured to be press-fitted within the intramedullary canal, and/or the stem 14 may be configured to be cemented within the cavity formed in the intramedullary canal. The proximal portion 16 may also have flutes 20 to inhibit rotation of the stem 14 within the intramedullary canal. Alternatively, the proximal portion 16 may have a smooth exterior surface, which falls within the scope of the present disclosure. The distal portion 18 may include threads 22 to allow the stem 14 to be removably attached to the femoral component 12 as discussed more fully below. The threads 22 may be located on a distal most end of the distal portion 18, as illustrated in FIG. 1.

The femoral component 12 may have an anterior side 24 and a posterior side 26. An anterior flange 25 may extend upwardly from a boss 32 on the anterior side 24 of the femoral component 12. The anterior flange 25 may be configured to seat against an anterior cortex of a patient's femur. It will be understood that the anterior cortex may be surgically prepared for receiving the anterior flange 25 in a manner known to those skilled in the art. For example, a femoral cut guide (not illustrated) may be used to surgical prepare the anterior cortex of the femur to receive the anterior flange 25.

The femoral component 12 may also include a condylar portion 28 configured for engaging, or articulating with, a tibial component. The condylar portion 28 may be formed as a pair of condylar members 29 that may be connected by a support member 30 on the posterior side 26. The condylar members 29 may be joined together at the anterior flange 25 on the anterior side 24. It will be understood that alternative embodiments of the femoral component 12 may be formed without the support member 30 such that the pair of condylar members 29 are separated by a space, or that the pair of condylar members 29 may be joined together at the posterior side 26 in various different configurations known to those skilled in the art.

Figure 2:
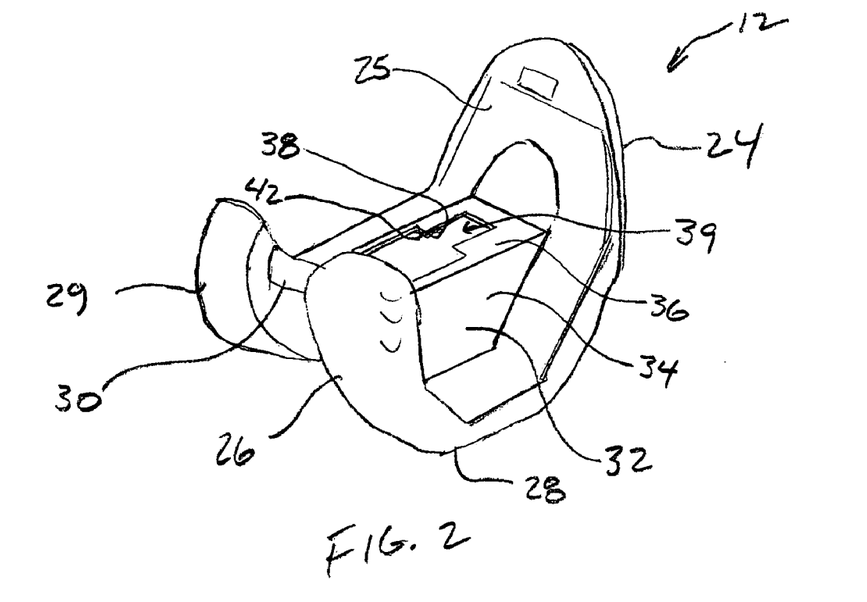
FIG. 2 is a perspective view of a femoral component of the prosthetic device of FIG. 1.
Figure 3:
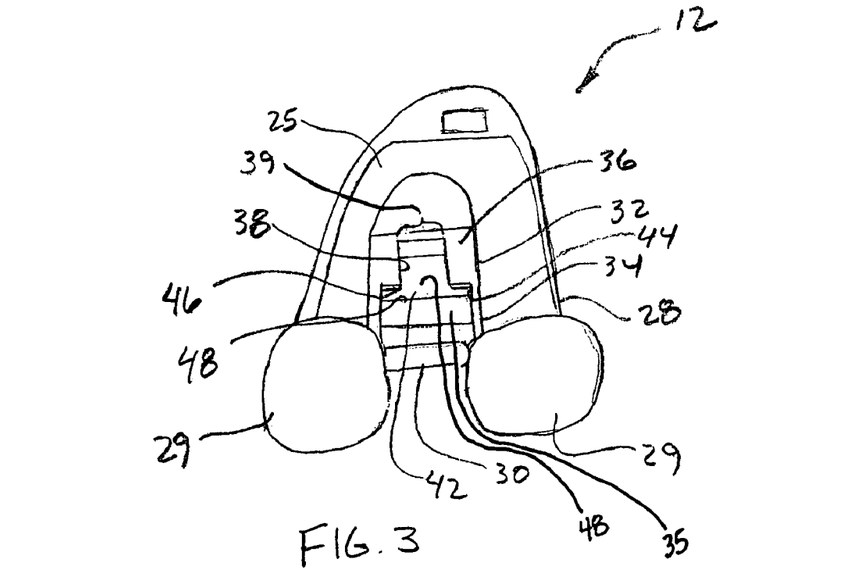
FIG. 3 is a front view of the femoral component of the prosthetic device of FIG. 1.

The femoral component 12 may also include the boss 32, referred to previously, also sometimes referred to as a box, positioned on an upper side of the condylar portion 28 between the condylar members 29. As shown most clearly in FIGS. 2-3, the boss 32 may include sidewalls 34 and a surface 36 extending between the sidewalls 34. It will be appreciated that surface 36 may extend entirely between the sidewalls 34, in other words may connect the sidewalls 34 together. Alternatively, as illustrated in FIGS. 2 and 3, the surface 36 may only extend partially between the sidewalls 34, such that there is a gap 39 formed within the surface 36, in other words the surface 36 may not connect the sidewalls 34 together. As illustrated in FIGS. 1 and 3, the boss 32 may or may not also include a lower support surface 35. When the lower support surface 35 is present as part of the boss 32, it may function to support the condylar members 29 and also may help to define an intercondylar notch, which is that portion of the femoral component 12 between each condylar member 29.

Figure 4:
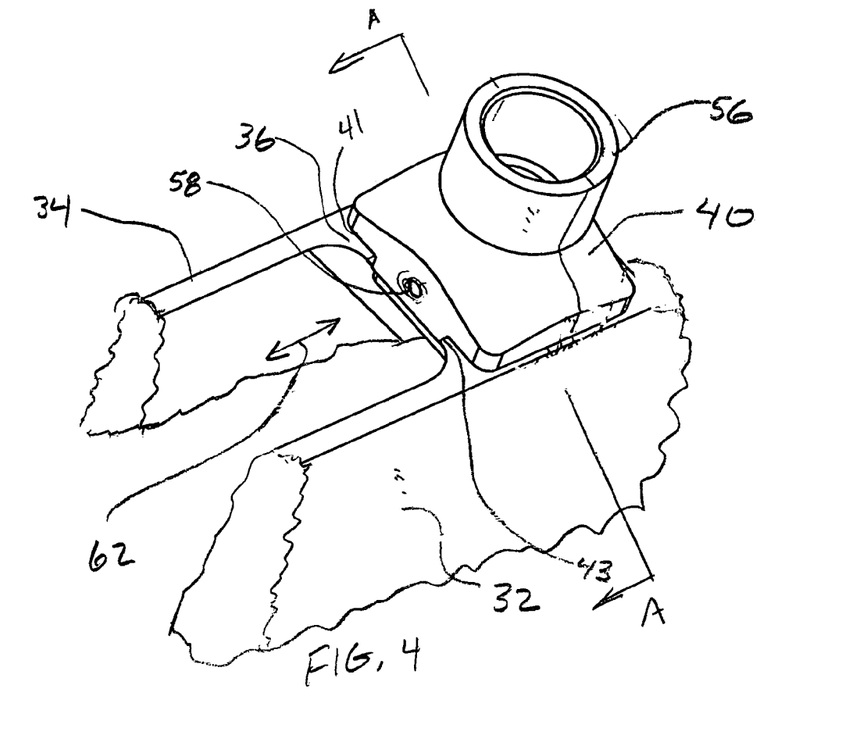
FIG. 4 is a break-away perspective view of a portion of the femoral component of FIG. 1 having a modular junction attached thereto.
Figure 5:
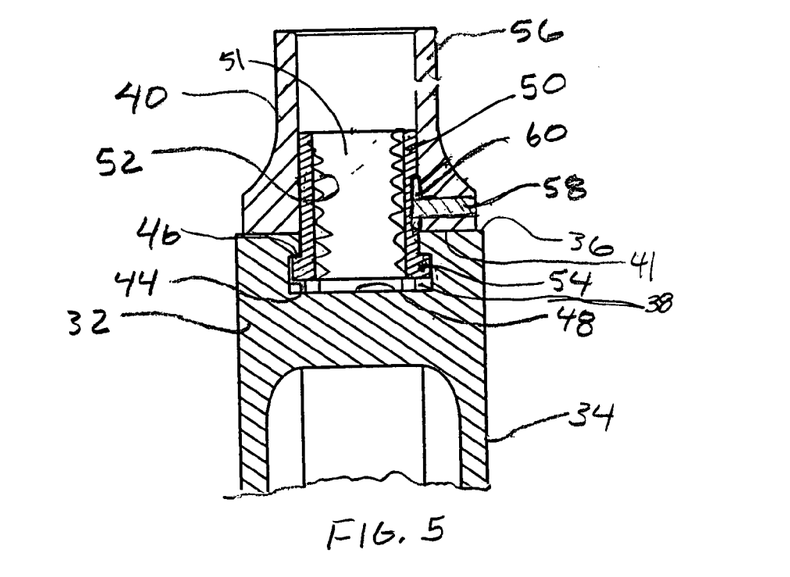
FIG. 5 is a cross-sectional view of the femoral component and modular junction of FIG. 4 taken along line A-A.

It will be appreciated that the boss 32 may be formed in various different shapes, sizes and configurations, which are within the scope of the present disclosure. The boss 32 may include a slot 38 for receiving a modular junction 40. As illustrated in FIGS. 2, 3, and 5, the slot 38 may be formed beneath the surface 36 of the boss 32, such that the slot 38 may be formed entirely beneath, or alternatively at least partially beneath, the surface 36. In other words, the slot 38 may undercut at least a portion of the surface 36. The slot 38 may form at least a portion of the gap 39 or space in the surface 36 for receiving the stem 14 therethrough as explained more fully below. As illustrated in FIGS. 1, 4 and 5, the stem 14 may be received in or through the gap 39 indirectly, in other words there may be intervening structure located between the stem 14 and the gap 39. For example, the modular junction 40 may surround, and be secured to, a portion of the stem 14, such that the modular junction 40 may be located between the stem 14 and the gap 39 or space thereby indirectly locating or receiving the stem 14 in or through the gap 39. Alternatively, the stem 14 may be directly received into or through the gap 39 or space, without any intervening structure located between the stem 14 and the gap 39 or space.

The gap 39 may be rectangular in shape, or alternatively, the gap 39 may have various other shapes, such as oval or other curved or linear shapes, and such other various shapes fall within the scope of the present disclosure. The slot 38 may have a slot opening 42 which may face the posterior side 26. Accordingly, the slot 38 may be configured to receive the modular junction 40 by movement of the modular junction 40 in the posterior to anterior direction, which movement is indicated by arrow 62 in FIG. 4.

In one embodiment of the present disclosure, as shown in FIG. 4, the modular junction 40 may include a planar lower surface 41 that may engage flush with the surface 36 of the boss 32. It will be appreciated that, as illustrated in FIG. 5, the flush engagement between the planar lower surface 41 with the surface 36 may occur on the top side of surface 36. This flush engagement may allow the modular junction 40 to be supported in a stable condition on the boss 32. Also, the modular junction 40 may include a guide 43 for contacting an edge of the slot 38 to prevent movement of the modular junction 40 in a medial lateral direction with respect to the femoral component 12. Alternatively, it will be understood that the modular junction 40 may include a connector 50, and said connector 50 may contact an edge of the slot 38 to prevent movement of the modular junction 40 in a medial lateral direction with respect to the femoral component 12 and to prevent movement toward or away from said femoral component.

As shown most clearly in FIG. 5, which shows a cross-sectional view of the boss 32 and the modular junction 40 taken along line A-A in FIG. 4, the slot 38 may include a recess 44 interposed between an overhang 46 and a floor 48. The slot 38 may be configured to receive the connector 50 to allow the modular junction 40 to be removably attached to the boss 32. The connector 50 may be a substantially cylindrical member having an opening 51 formed therein with threads 52 formed on the interior of the opening 51. It will be appreciated that the connector 50 may have other shapes other than substantially cylindrical, for example square, oblong, oval, polygonal shapes or other geometric shapes. A rim 54 may be formed on the connector 50 to form a protruding portion of the connector 50. As illustrated in FIG. 3, the floor 48 may be connected to the lower support surface 35, when present, and may form a barrier such that the slot 38 may be inaccessible from beneath the femoral component 12. The inaccessibility of the slot 38 from beneath the femoral component 12 may be due, at least in part, to the presence of the lower support surface 35 of the boss 32. Accordingly, in one embodiment of the present disclosure, the prosthetic device 10 may be characterized by an absence of fastening mechanisms extending from beneath the femoral component 12 for attaching the stem 14.

The modular junction 40 may include a sleeve 56 configured for receiving at least a portion of the connector 50 for removable attachment to the stem 14. The connector 50 may be sized and shaped to move or float within the sleeve 56. The connector 50 may be removably attached to the sleeve 56 of the modular junction 40 by means of a connecting device such as a pin 58. The connector 50 may also include a groove or recess 60 or area of reduced diameter for receiving the pin 58. It will be understood that the connector 50 may be allowed to move with respect to the sleeve 56 until the pin 58 contacts the ends of the groove or recess 60. This may allow the connector 50 to be movably attached to the modular junction 40 so that the connector 50 may remain in place to prevent separation of the connector 50 from the modular junction 40 to facilitate use in surgery. Moreover, the pin 58 may be used to prevent the connector 50 from rotating beyond a desired point with respect to the sleeve 56. It will be understood that the pin 58 may be positioned in various locations on the modular junction 40, and the pin 58 may engage the sleeve 56 in any suitable manner, such as in a loose fit, or in a compression fit, or a taper fit, or in threaded engagement, or with adhesive, or in any suitable bond or other connection, and any number of pins 58 may be used. It will also be appreciated that other connecting devices besides the pin 58 may be used within the scope of the present disclosure to allow the connector 50 to be joined to sleeve 56 of the modular junction 40. Such connecting devices may include devices such as threaded T nuts, fasteners, or clips for example, and may form a means for movably attaching the connector 50 to the modular junction 40.

It will be appreciated that an alternative embodiment of the present disclosure, not shown, may include the connector formed as a threaded rod member, and the distal portion 18 of the stem 14 may be configured as a cylinder with a threaded interior surface. Accordingly, the threaded rod connector may be received in the cylindrical stem in a manner opposite to that shown in FIGS. 1 and 5.

Figure 6A:
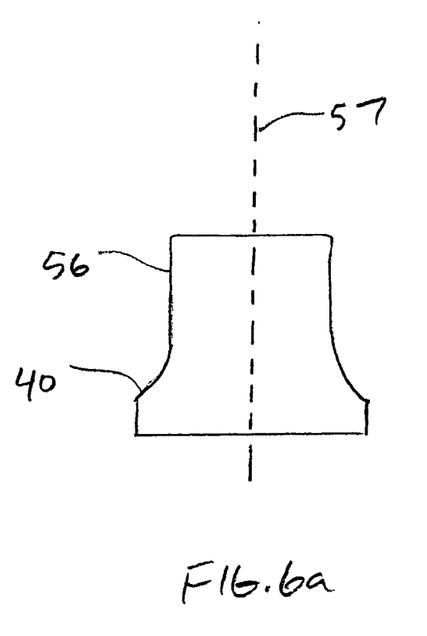
FIG. 6a is a side view of a modular junction extending in a first direction.
Figure 6B:
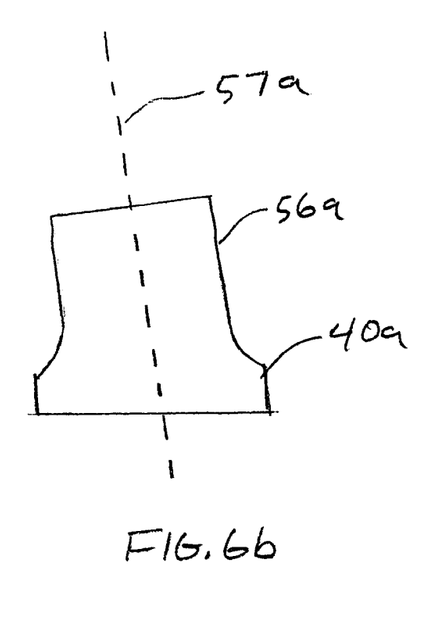

It will be understood that modular junctions 40 may be configured with sleeves 56 in various different positions and angles, as is shown most clearly in FIGS. 6a and 6b. The modular junction 40 may have a sleeve 56 extending in a first direction 57 as depicted by the dashed line in FIG. 6a. FIG. 6b shows a second modular junction 40a having a sleeve 56a extending in a second direction 57a at an angle with respect to the first direction 57. It will be understood that modular junctions may be configured at various other angles within the scope of the present disclosure to be suitable for a particular patient. Accordingly, a particular modular junction 40 may be selected having the sleeve 56 configured and oriented as desired to achieve the desired angle of the stem 14. Thus, a single femoral component 12 and stem 14 can be assembled in various different angular configurations, depending upon the particular modular junction 40 used.

In use, the femur may be surgically prepared for receiving the prosthetic device 10 in a manner known in the art. It will be understood that the prosthetic device 10 may be used in primary or revision knee replacement procedures. A stem 14 may be selected having a suitable size for the patient, and a modular junction 40 corresponding to the stem 14 may also be selected to provide the desired angle of attachment of the stem 14. The modular junction 40 may be placed between the condylar members 29 near the posterior side 26 between the slot opening 42 and the support member 30 of the femoral component 12. The modular junction 40 may then be moved toward the anterior side 24 so that the connector 50 may be received within the slot 38, e.g., in a posterior to anterior direction. The rim 54 of the connector 50 may be positioned in the recess 44, such that the modular junction 40 may be allowed to slide along the surface 36 of the boss 32 to the desired position to be properly fitted for a particular application. The modular junction 40 may be allowed to move in a translation movement in the posterior-anterior direction as shown by the arrow 62 in FIG. 4 to allow the femoral component 12 to be positioned such that the anterior flange 25 seats firmly against the anterior cortex of the femur. The stem 14 may be inserted into the sleeve 56 to engage the stem threads 22 with the connector threads 52. The stem, 14 may be rotated or screwed to cinch the connector 50 so that the rim 54 of the connector 50 contacts the overhang 46 formed in the boss 32, and the lower planar surface 41 of the modular junction contacts the surface 36 of the boss 32. As the stem 14 is tightened, the modular junction 40 may be fixed in place with respect to the boss 32 of the femoral component 12. Thus, it will be appreciated that the stem 14 may be adjustably fixed to the femoral component 12 by a single threaded engagement, and that the modular junction 40 may be fixed to the femoral component 12 in an infinite number of positions along the anterior to posterior direction of the slot 38.

It will be understood that other embodiments within the scope of the present disclosure may utilize stops or other such features to allow the modular junction 40 to be adjusted to discrete positions with respect to the boss 32. For example, stops may be formed in either the modular junction 40 or the boss 32 to allow fixing of the modular junction 40 with respect to the boss 32 only in certain positions, rather than at an infinite number of positions.

It will also be appreciated that in one embodiment, the stem 14 may be configured to contact the floor 48 of the slot 38 to enable the threaded engagement of the stem 14 and the connector 50 to force the rim 54 into contact with the overhang 46. Alternatively, it will be appreciated that the stem 14 may be configured with a ledge (not shown) that may contact the top of the sleeve 56 such that rotation of the stem 14 causes movement of the connector 50 with respect to the stem 14 to create a compressive force between the rim 54 and the ledge on the stem 14.

It will be appreciated that in the following embodiment similar reference numerals will be used wherever possible to indicate like structural features with respect to the previous embodiment. More specifically, it is noted that in FIGS. 7-8, the following embodiment is explained and described with the use of pre-existing reference numerals that are increased by a sum of "100" compared to reference numerals referring to similar features shown in FIGS. 1-6, to thereby distinguish the following embodiment from the previous embodiment. For example, a lower support surface in the previous embodiment has been given reference numeral 35 and the same or corresponding structural feature in the following embodiment of the lower support surface has been given a reference numeral 135.

Figure 7:
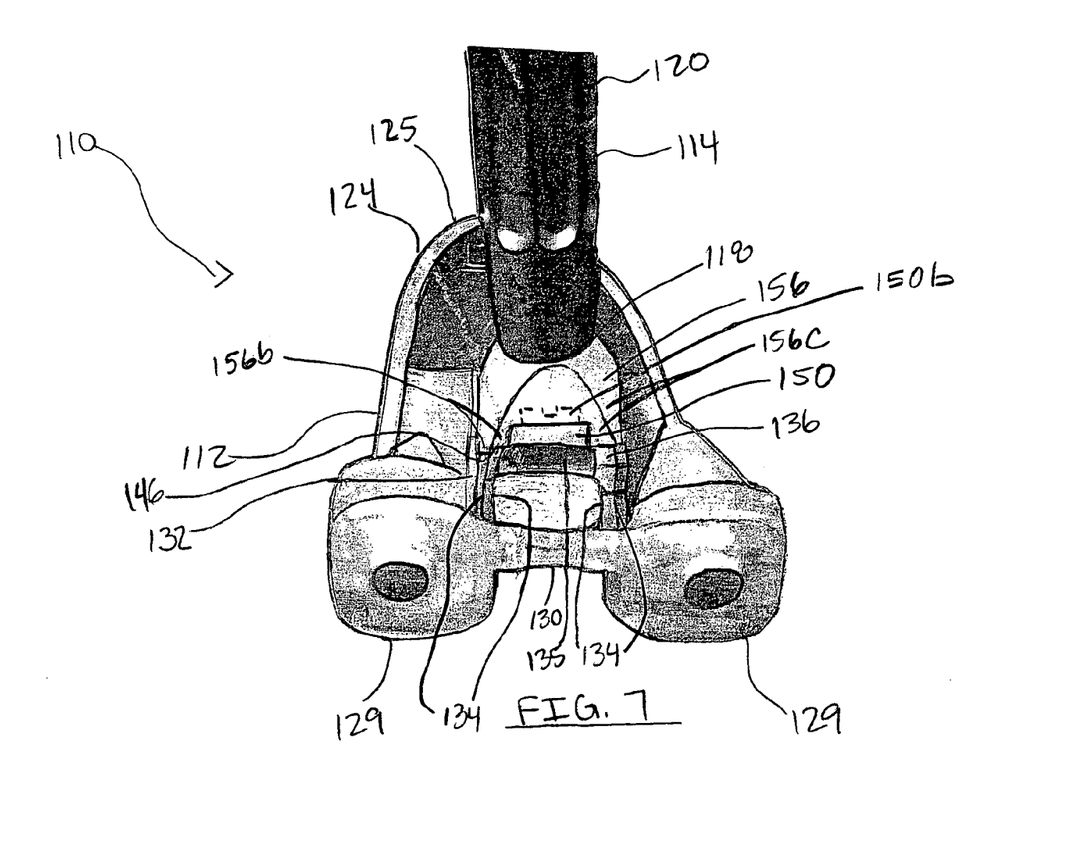
FIG. 7 is a front view of the femoral component of the prosthetic device used in conjunction with an alternative embodiment of a modular junction.
Figure 8:
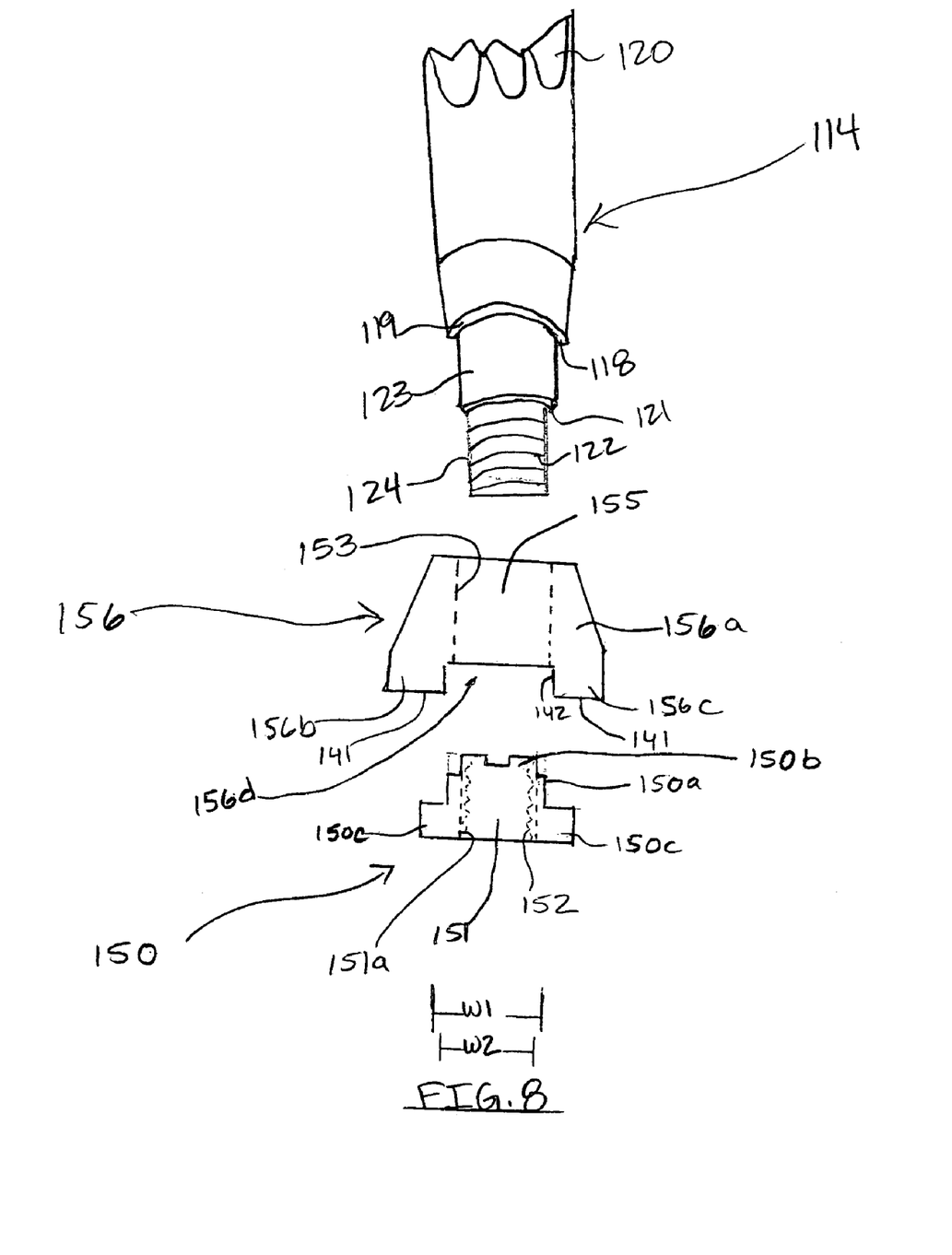
FIG. 8 is an exploded side view of a stem and the modular junction illustrated in FIG. 7.

Referring now to FIGS. 7 and 8, an alternative embodiment of a modular junction 140 is illustrated, and may include a sleeve 156 and a connector 150, which together may form a double-nut. The connector 150 may itself be, roughly speaking, T-shaped and may comprise a base 150a that may form the foundation of the connector 150. The connector 150 may further comprise an extension 150b that may be hollow and that may protrude outwardly from a top of the base 150a of the connector 150 in an upward manner with respect to the entrance of the stem 114 into the modular junction 140. The connector 150 may also include at least one laterally extending member 150c that may extend laterally outward from the base 150a, and more specifically may comprise two laterally extending members 150c, as illustrated in FIG. 8. The laterally extending members 150c may form the top portion of the T-shape of the connector 150.

It is to be understood that the sleeve 156 of the present embodiment may be removably attached to the connector 150 of the modular junction 140, however, such removable attachment may be performed with or without a connecting device such as a pin 58. It will therefore be appreciated that the sleeve 156 and connector 150 of the present embodiment may be modified to include a connecting device, such as a pin 58, but such a connecting device is not required by the present embodiment of the modular junction 140. Still further, the embodiment shown in FIGS. 1-6 may, if desired, be manufactured to eliminate, or include, the presence of pin 58, as desired.

It will be appreciated that the extension 150b may be columnar shape, or it may be square, polygonal or some other shape without departing from the scope of the present disclosure. An opening 151 defined by a sidewall 151a may extend through the connector 150 from the top of the extension 150b to the bottom of the base 150a. It will be appreciated that the extension 150b may be axially aligned with, and may form part of, the opening 151 (shown in phantom line in FIG. 8). The sidewall 151a defining the opening 151 may comprise threads 152. The opening 151 may extend through the center or middle of the base 150a, and may be open at both ends of the connector 150. The threaded sidewall 151a may be configured and dimensioned to matingly engage a corresponding set of threads 122 located on a distal end 118 of a stem 114.

The sleeve 156 illustrated in FIGS. 7 and 8, on the other hand, may include a main block portion 156a having two legs 156b and 156c that may extend outwardly therefrom in a downward, axial manner with respect to the entrance of the stem 114 into the modular junction 140. The legs 156b and 156c may each have a base or a lower portion 141, also referred to herein as a rim of the sleeve 156, and inner portions 142. The sleeve 156 may also comprise a sidewall 153 defining an opening 155. The opening may extend through the sleeve 156, as illustrated by the phantom lines in FIG. 8.

Further, the sleeve 156 may comprise a recessed area 156d located between the legs 156b and 156c. The recessed area 156d may have a width W1 that may be defined by the distance between the inner portions 142 of the legs 156b and 156c, where the width W1 may be wider than a corresponding width W2 of the base 150a. The recessed area 156d may therefore allow the extension 150b and the base 150a to pass by the legs 156b and 156c without substantial interference therebetween. It is to be understood that the inner portions 142 of the legs 156b and 156c may contact and engage a surface of the base 150a. It will be appreciated that to provide an appropriate fit between the base 150a and the inner portions 142 of the legs 156b and 156c, the width W1 may be slightly larger than the width W2 such that a snug fit, with some amount of contact and engagement may occur. In other words, width W1 may be substantially the same as width W2, with W1 being only slightly larger than W2 to allow the base 150a to enter into the recessed area 156d and potentially contact the inner portions 142 of the legs 156b and 156c.

The sleeve 156 and the connector 150 may be brought into engagement with each other, and when that engagement occurs the opening 155 of the sleeve 156 may be in axial alignment with the opening 151 of the connector 150. When the sleeve 156 may be brought into engagement with the connector 150, the extension 150b may be used as a guide to aid in the insertion process. The extension 150b may act as a guide because it may be insertable into the opening 155 of the sleeve 156 for increasing the ease of installation. It will be appreciated that the opening 155 of the sleeve 156 may be larger in diameter than the diameter of the opening 151 of the connector 150. The purpose of the relative sizes of the openings 151 and 155 will be discussed further below.

Referring now to the stem 114, a first portion 123 may extend from or near the distal end 118 of the stem 114, and a second portion 124 may extend from the first portion 123. The first and second portions 123 and 124 may both be columnar in shape as illustrated in FIG. 8. However, it will be appreciated that the shape of the first and second portions 123 and 124 may be modified and other shapes may be utilized for the shape of the first and second portions 123 and 124 without departing from the scope of the present disclosure, but such shapes should compliment the shape of the openings 155 and 151, respectively. A first rim 119 may be formed at the base of the distal end 118 of the stem 114 from which the first portion 123 may extend. A second rim 121 may be formed at the base of the first portion 123 from which the second portion 124 may extend.

It will be appreciated that the second portion 124 may have a narrower diameter than the first portion 123, such that the second portion 124 may pass through the opening 155 of the sleeve 156 in order to be inserted into the opening 151 of the connector 150. Further, the diameter of the opening 151 of the connector 150 may be substantially the same as the diameter of the second portion 124 of the stem 114. The second portion 124 may comprise threads 122 that may matingly engage the threads 152 of the sidewall 151a of the opening 151 of the connector 150. The sidewall 151a of the opening 151 may engage the second portion 124 in a threaded engagement to secure the modular junction 140 to the stem 114.

Additionally, the diameter of the first portion 123 of the stem 114 may be substantially the same as the diameter of the opening 155 of the sleeve 156. It is to be understood that the first portion 123 may enter into the opening 155 and the outer surface of the first portion 123 may engage the sidewall 153 of the opening 155 to provide the desired fit therebetween.

The threaded engagement between the second portion 124 and the sidewall 151a of the opening 151 may allow the stem 114 to be tightened and loosened with respect to the modular junction 140 through screwing, or unscrewing, the second portion 124 of the stem 114 into, or out of, the threaded opening 151 of the connector 150. The threaded engagement between the connector 150 and the second portion 124 of the stem 114 may be such that a clamping action may occur between the laterally extending members 150c of the connector 150 and the base 141 of the legs 156b and 156c. Specifically, a channel or groove may be formed between the two laterally extending members 150c of the connector 150 and the base 141 of the two legs 156b and 156c of the connector when the connector 150 and the sleeve 156 may be assembled together. Accordingly, as the stem 114 may be tightened or loosened with respect to the modular junction 140 the laterally extending members 150c and the base 141 of the two legs 156b and 156c may clamp onto surface 136, which may be formed as part of the boss 132. In other words, surface 136 may be clamped between the laterally extending members 150c and the base 141 of the two legs 156b and 156c, as illustrated in FIG. 7.

The clamping between the laterally extending members 150c and the base 141 allow the modular junction 140 to slide across surface 136 in an anterior/posterior direction (the anterior/posterior direction is in reference to the patient's body when the femoral component is located in the patient's femur). During the sliding of the modular junction 140 along surface 136 and subsequent tightening or clamping thereto, the sleeve 156 may reside above the surface 136 and a portion of the connector 150 may reside below the surface 136, as illustrated in FIG. 7.

It will be appreciated that the above structure may allow the stem 114 to be secured to the boss 132 via the modular junction 140. Further, the above structure may advantageously allow movement between the stem 114 and the boss 132 through an infinite number of positions in the anterior/posterior direction (A/P direction), i.e., toward or away from condyles 129, by sliding the modular junction 140 in the anterior/posterior (A/P) direction along the groove or slot 138 formed beneath the surface 136. The sleeve 156 of the modular junction 140 may also be configured and dimensioned such that it may offset the stem 114 relative to the femoral component 112. To accomplish the offset, the base 141 of the legs 156b and 156c may be formed such that one leg, for example 156b, may be larger or longer than the other leg, for example 156c. It will also be appreciated that the stem 114 may be modular and may be selected from a wide ranging group of various stems 114 to accommodate the differing bone anatomies of a wide of patients.

It will be understood that the components of the present disclosure may be formed of various different materials known in the art suitable for prosthetic devices.

It will be appreciated that the structure and apparatus disclosed herein is merely one example of a means for moveably attaching the connector to the modular junction, and it should be appreciated that any structure, apparatus or system for attaching which performs functions the same as, or equivalent to, those disclosed herein are intended to fall within the scope of a means for moveably attaching the connector to the modular junction, including those structures, apparatus or systems for attaching which are presently known, or which may become available in the future. Anything which functions the same as, or equivalently to, a means for moveably attaching falls within the scope of this element.

In accordance with the features and combinations described above, a useful method of assembling a prosthetic device is disclosed. The prosthetic device includes a femoral component, a modular junction and a stem, the method includes the steps of:

(a) joining the modular junction to the femoral component;
(b) adjusting the modular junction in an anterior-posterior direction with respect to the femoral component; and
(c) fixing the modular junction with respect to the femoral component by turning the stem in the modular junction.

Those having ordinary skill in the relevant art will appreciate the advantages provide by the features of the present disclosure. For example, it is a feature of the present disclosure to provide a prosthetic device which is simple in design, manufacture and use. Another feature of the present disclosure is to provide such a prosthetic device capable of allowing attachment of a stem through a modular junction that is adjustable through infinite positions in the anterior-posterior direction. It is a further feature of the present disclosure, in accordance with one aspect thereof, to provide a knee prosthesis that allows adjustable connection of a stem with a single threaded engagement. It is another feature of the present disclosure to provide a modular femoral knee stem extender having a minimal number of pieces. It is a further feature of the present disclosure to provide a prosthetic device that allows connection of a stem to a femoral component in various different angles. It is an additional feature of the present disclosure to provide a prosthetic device that reduces the quantity of inventory required to fit the needs of numerous anatomical configurations.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A prosthetic device comprising:
   a femoral component having an anterior side, a posterior side, a condylar portion and a boss, said boss comprising a slot;
   a modular junction receivable in said slot for attaching a stem to said femoral component, said modular junction being adjustably attachable in position relative to said femoral component to thereby allow translational movement of said stem through infinite positions in opposing directions, said modular junction being configured and arranged such that engagement of the stem to said modular junction thereby causes said modular junction to be secured to said femoral component in any of the infinite positions.

2. The device of claim 1, wherein said slot has an opening facing said posterior side such that said slot receives said modular junction by moving said modular junction in a posterior to anterior direction.

3. The device of claim 1, wherein said slot is inaccessible from beneath said femoral component.

4. The device of claim 3, wherein the inaccessibility of said slot is due, at least in part, to a lower support surface formed as part of the boss.

5. The device of claim 1, wherein said slot comprises an overhang.

6. The device of claim 1, wherein said connector comprising a rim.

7. The device of claim 1, wherein said connector comprises a cylindrical member having an opening with threads formed on an interior thereof for engaging with said stem.

8. The device of claim 6, wherein said rim engages with an overhang to fix said modular junction with respect to said femoral component when said stem is connected to said connector.

9. The device of claim 1, wherein said modular junction comprises means for moveably attaching the connector to the modular junction.

10. The device of claim 9, wherein said means for moveably attaching the connector to the modular junction comprises a pin.

11. The device of claim 1, wherein said stem is configured and dimensioned for attachment to a femur.

12. The device of claim 11, wherein a distal portion of said stem is threaded.

13. The device of claim 1, wherein said condylar portion comprises a pair of condylar members.

14. The device of claim 13, further comprising a support member connecting said pair of condylar members on said posterior side.

15. The device of claim 1, wherein said boss comprises sidewalls and a surface extending between said sidewalls.

16. The device of claim 15, wherein said slot is formed beneath said surface of said boss.

17. The device of claim 1, wherein said slot comprises a recess interposed between an overhang and a floor.

18. The device of claim 1, wherein said modular junction comprises a guide for contacting an edge of said slot to prevent movement of said modular junction in a medial lateral direction with respect to said femoral component.

19. The device of claim 1, wherein the modular junction further comprises a connector having an opening defined by a sidewall.

20. The device of claim 19, wherein the sleeve comprises an opening defined by a sidewall, and wherein the opening of the connector and the opening of the sleeve each have a diameter, and wherein the diameter of said opening of said sleeve is larger than the diameter of said opening of said connector.

21. The device of claim 1, wherein said slot is formed between an overhang of the boss and a floor of a lower support surface of said boss.

* * * * *